(12) United States Patent
Laikhter et al.

(10) Patent No.: US 8,618,279 B2
(45) Date of Patent: Dec. 31, 2013

(54) SYNTHESIS OF 2',3'— AND 3',5'—CYCLIC PHOSPHATE MONO-AND OLIGONUCLEOTIDES

(75) Inventors: Andrei Laikhter, Lexington, MA (US); Suresh Chandra Srivastava, Burlington, MA (US); Naveen Srivastava, Burlington, MA (US)

(73) Assignee: ChemGenes Corporation, Wilmington, MA (US)

( * ) Notice: Subject to any disclaimer, the term of this patent is extended or adjusted under 35 U.S.C. 154(b) by 808 days.

(21) Appl. No.: 12/657,227

(22) Filed: Jan. 15, 2010

(65) Prior Publication Data
US 2011/0009606 A1 Jan. 13, 2011

Related U.S. Application Data (60) Provisional application No. 61/205,100, filed on Jan. 15, 2009.

(51) Int. Cl.
*C07H 19/20* (2006.01)
(52) U.S. Cl.
USPC ........................................................ 536/26.13
(58) Field of Classification Search
None
See application file for complete search history.

(56) References Cited

U.S. PATENT DOCUMENTS 7,547,775 B2 *  6/2009  Kuimelis et al. .............. 536/25.3

OTHER PUBLICATIONS

Vyle et al., "A Novel Support for Synthesis of 2',3'-cyclic phosphate Terminated Oligonucleotides," Tetrahedron Letters, 39(43), 7975-7978 (Oct. 22, 2998).*

* cited by examiner

*Primary Examiner* — Lawrence E Crane
(74) *Attorney, Agent, or Firm* — Law Offices of Indu M. Anand; Indu M. Anand, Esq.

(57) ABSTRACT

The invention provides a novel method for the chemical synthesis of 2',3'-cyclic phosphate and phosphorothioate of mono and terminated oligonucleotides synthesis. The invention also provides a novel method of for the chemical synthesis of 2',3'- and 3',5'-cyclic phosphate and phosphorothioate mononucleotide nucleotides. The process is based on quick and efficient cyclization of phosphoramidate moiety and neighboring hydroxyl group. The present invention is directed towards the synthesis of high purity DNA and RNAs, specifically to introduce cyclic phosphate at 3'-end of oligonucleotides. Such DNA and RNA's have extensive application in therapeutics, diagnostics, drug design, and selective inhibition of an RNA sequence within cellular environment, in pre-tRNA cleavage and in ribozyme ligation. The 2',3'-cyclic phosphate nucleosides are involved in a vast number of applications in molecular biology in general and mammalian cells in particular. The invention also envisions providing kits comprising at least one composition disclosed in the present invention.

9 Claims, 4 Drawing Sheets

FIG. 1 ESI Mass spectrum of oligonucleotide SEQ ID No. 2.

FIG 2 HPLC Analysis of adenosine 2',3'-cyclic monophosphate, authentic sample.

FIG 3 HPLC Analysis of adenosine 2',3'-cyclic monophosphate, synthesized using solid support 1b.

FIG 4 HPLC Analysis of adenosine 2',3'-cyclic monophosphate, co-migration experiment.

SEQUENCE LISTING

<160> NUMBER OF SEQ ID NOS: 4

<210> SEQ ID NO 1
<211> LENGTH: 10
<212> TYPE: DNA
<213> ORGANISM: Artificial Sequence
<220> FEATURE:
<223> OTHER INFORMATION: Completely Synthesized
<220> FEATURE:
<221> NAME/KEY: misc_feature
<222> LOCATION: (10)..(10)
<223> OTHER INFORMATION: 2',3'-Cyclic phosphate

<400> SEQUENCE: 1
tttttttttu                                                          10

<210> SEQ ID NO 2
<211> LENGTH: 20
<212> TYPE: DNA
<213> ORGANISM: Artificial Sequence
<220> FEATURE:
<223> OTHER INFORMATION: Completely Synthesized
<220> FEATURE:
<221> NAME/KEY: misc_feature
<222> LOCATION: (20)..(20)
<223> OTHER INFORMATION: 2',3'-Cyclic phosphate

<400> SEQUENCE: 2
tttttttttt tttttttttu                                               20

<210> SEQ ID NO 3
<211> LENGTH: 13
<212> TYPE: DNA
<213> ORGANISM: Artificial Sequence
<220> FEATURE:
<223> OTHER INFORMATION: Completely Synthesized
<220> FEATURE:
<221> NAME/KEY: misc_feature
<222> LOCATION: (1)..(11)
<223> OTHER INFORMATION: 2'-O-Methyl
<220> FEATURE:
<221> NAME/KEY: misc_feature
<222> LOCATION: (13)..(13)
<223> OTHER INFORMATION: 2',3'-Cyclic phosphate

```
<400> SEQUENCE: 3
acuuguugac auu                                                          13

<210> SEQ ID NO 4
<211> LENGTH: 20
<212> TYPE: DNA
<213> ORGANISM: Artificial Sequence
<220> FEATURE:
<223> OTHER INFORMATION: Completely Synthesized
<220> FEATURE:
<221> NAME/KEY: misc_feature
<222> LOCATION: (20)..(20)
<223> OTHER INFORMATION: 2',3'-Cyclic phosphate

<400> SEQUENCE: 4
tttttttttt tttttttttg                                                   20
```

SYNTHESIS OF 2',3'— AND 3',5'—CYCLIC PHOSPHATE MONO-AND OLIGONUCLEOTIDES

CROSS REFERENCE TO RELATED APPLICATIONS

This application claims priority from U.S. provisional patent application Ser. No. 61/205,100, filed by the inventors on Jan. 15, 2009. The entire contents of the prior application are herein incorporated by reference.

FIELD OF THE INVENTION

This application pertains to the methods of synthesis of 2',3'-, 3',5'-cyclic phosphate mono nucleosides and 2',3'-cyclic phosphate terminated oligonucleotides. It also discloses several solid support compositions that can be utilized in the synthesis of desired 2',3'-, 3',5'-cyclic phosphate mono nucleosides and 2',3'-cyclic phosphate terminated oligonucleotides.

BACKGROUND OF THE INVENTION

Cyclic phosphate mono nucleosides and cyclic phosphate terminated oligonucleotides play an important role in the living cell. The 3',5'-cyclic guanosine monophosphate (GMP) is involved in the light activation of $Na^+$ cell channels (Molecular Cell Biology $3^{rd}$ edition, 1995). The 2',3'-cyclic phosphate nucleotides are involved in tRNA exons repair process in mammalian cells (Schwer, B., Aronova, A., Ramirez, A., Braun, P., and Shuman, P. (2008) *RNA*, 14, 204-210). Approximately 90% of human U6 small nuclear RNA (snRNA) contains uridine cyclic phosphate (U>p) at its 3'-end (Lund, E., and Dahlberg, J. E. (1992) *Science* 255, 327-330). Furthermore, 2',3'-cyclic phosphate terminated RNAs have been characterized as products relating to a wide variety of biological processes; including small ribozyme autolysis pre-tRNA cleavage, small nuclear RNA 3'-uridylation, and the initial products in ribonuclease mediated RNA cleavage. Synthetic 2',3'-cyclic phosphates were first utilized in 1952 to help identify the products from incomplete RNase digestion of RNA and have since facilitated mechanistic studies on ribozyme ligation and both chemical and enzymatic, cleavage of RNA.

The synthesis of all of the classes of oligonucleotides having a terminal cyclic phosphate, can now be achieved with the combination of oligonucleotide synthesis methodology and the technology of cyclic phosphate synthesis of the present invention.

The synthesis of 2',3'-cyclic monophosphate nucleostides is well established using dicyclohexylcarbodiimide (Smart, J., Synthetic Procedures in Nucleic Acid Chemistry by Kochetkov, N. K. and Budovskii, E. I., pp. 487-490, Plenum Press, 1972) or acetic anhydride (Stuart, A. and Khorana, H. G. (1963) *J. Am. Chem. Soc.* 85, 2346; Stuart, A. and Khorana, H. G. (1964) *J. Biol. Chem.* 239, 3885). However, these methods cannot be applied for the oligonucleotides because of extensive phosphate backbone in the oligonucleotides. The enzymatic method of 2',3'-cyclic monophosphate nucleotides employs corresponding nucleotide cyclases, which convert 3'monophosphate nucleotides into their 2',3' cyclic form. Additionally, cyclic phosphates have been prepared by solution phase reaction such as ribozyme cleavage, phosphitylation, and phosphate coupling.

The ability to prepare cyclic phosphate terminated oligonucleotides on solid support would dramatically improve the capabilities to synthesize a vast variety of oligonucleotides with terminal cyclic phosphate function. This will greatly enhance applications of such oligonucleotides, both in the study of biological processes involving these moieties and also in generating nucleic acid libraries with ligating activity. A process for making 2,3, cyclic phosphate oligonucleotides via solid support was first published by Vyle, J. S., Williams N. H. and Grasby Jane A., *Tetrahedron Letters* 39,7975-7978, 1998.

In order to make 2',3'-cyclic monophosphate oligonucleotide Vyle and coworkers prepared O,S-dialkyl 3'-O-nucleosidyl phosphorothioate triesters and attached those synthons to the solid support (Vyle, J. S., Wiliams, N H. and Grasby, J. A. (1998) *Tetrahedron Lett.* 39, 7975-7978). The process involved utilization of standard ribonucleosidecyanoethylphosphoramidite having a 2'-O-Fpmp protected uridine nucleoside (compound 1), which was converted in situ to O-trimethylsilyl-cyanoethyl phosphate uridine (compound 2), and without isolation treated to a solid support bound disulfide (compound 5), leading to solid support bound O-S-dialkylphosphorothiolate (compound 3). Selective removal of Fpmp group produced compound 4. The authors subsequently treated compound 4 with iodine, to result in a cyclic phosphate, compound 6. O-S-dialkylphosphorothiolate, (compound 2), using a solid support bound disulfide (compound 5) resulting in solid support compound 3.

Compound 5

Compound 6

Although in their process the iodine mediated loss of sulfur, followed by cyclization of neighboring oxygen, results in cyclic phosphate and liberates an oligonucleotide, Vyleet al. did not reveal the yield and the quality of the terminal cyclic phosphate attached pentamer synthesized by the process. The process was only applied to synthesize a pentamer having pyrimidine bases. No long chain oligonucleotides having mixed bases of all four nucleosides were reported by the authors. Furthermore, the process utilizes Fpmp protection on neighboring hydroxyl of the ribose nucleoside.

The Fpmp protecting group has serious limitations in oligonucleotide synthesis and chain elongation of oligoribo nucleotides and that leads to poor quality of oligonucleotides due to lower coupling efficiency per step. Our invention presented herein, on the other hand, provides an elegant process of wide practical application to produce high quality oligonucleotides having a terminal cyclic phosphate moiety.

With the present invention, it is possible to synthesize various classes of defined sequence RNA molecules in the 3',5' direction, and use them for the synthesis and development of a vast variety of therapeutic grade RNA aptamers, tRNA's, siRNA, and biologically active RNA molecules. This approach utilizes a conventional phosphoramidite monomer having 2'-t-Butyldimethylsilyl ether protecting group and 5' dimethoxytrityl (DMT) protection.

The oligoribo nucleotide and oligodeoxyribonucleotide molecules can both be synthesized using the solid support of the present invention. Subsequent to synthesis on the support, the base protecting groups on the oligodeoxy nucleotide or oligoribonucleitide can be deprotected safely while the solid support is still bound with the latent cyclic phosphate moiety at the terminal.

The general process for oligonucleotide synthesis (scheme 1) has been elegantly described by various research groups, now for over past 25 years. (Ogilvie, K. K., *Can. J. Chem.*, 58, 2686, 1980 (scheme 1). The 2'-silyl ethers as protecting group have been developed extensively and they are known to have remarkable stability. Solvolysis of silyl ethers have been extensively studied and that bulky alkyl silyl ethers have a high degree of stability, (Bazani, B and Chvalowski, V, Chemistry of Organosilicon compounds, Vol. 1, Academic Press, New York, 1965). Extensive research work was subsequently done by Ogilvie and coworkers as 2'-hydroxy protecting group for oligoribonucleotide synthesis (Ogilvie, K. K., Sadana, K. L, Thompson, E. A., Quilliam, M. A., and Westmore, J. B *Tetrahedron Letters*, 15, 2861-2864, 1974; Ogilvie, K. K., Beaucage, S. L, Entwistle, D. W., Thompson, E. A., Quilliam, M. A., and Westmore, J. B., *J. Carbohydrate Nucleosides Nucleotides*, 3, 197-227, 1976; Ogilvie, K. K. Proceedings of the 5th International Round Table on Nucleosides, Nucleotides and Their Biological Applications, Rideout, J. L., Henry, D. W., and Beacham L. M., III, eds., Academic, London, pp. 209-256,1983). These studies subsequently led to continued developments of methods which were amenable to both solution and solid phase oligonucleotide synthesis;, and the first chemical synthesis of RNA molecules of the size and character of tRNA (Usman, N., Ogilvie, K. K., Jiang, M.-Y., and Cedergren, R. J. *J. Am. Chem. Soc.* 109, 7845-7854, 1987; Ogilvie, K. K., Usman, N., Nicoghosian, K, and Cedergren, R. J. *Proc. Natl. Acad. Sci. USA*, 85, 5764-5768, 1988; Bratty, J., Wu, T., Nicoghosian, K., Ogilvie, K. K., Perrault, J.-P., Keith, G. and Cedergren, R., *FEBS Lett.* 269, 60-64, 1990).

The literature has been amply reviewed in subsequent excellent publications: Gait, M. J., Pritchard, C. and Slim, G., Oligonucleotides and Their Analogs: A Practical Approach (Gait, M. J., ed.), Oxford University Press Oxford, England, pp. 25-48, 1991.

The synthesis of all of the classes of oligonucleotides described above, in addition having a terminal cyclic phosphate, can now be achieved with the combination of oligonucleotide synthesis methodology and the technology of cyclic phosphate synthesis of the present invention.

For the synthesis of oligonucleotide chain having a terminal cyclic phosphate, other protecting groups besides silyl ether protecting group have been lately employed for RNA synthesis. Examples include bis (2-acetoxyethyl-oxy) methyl (ACE), Scaringe, S. A., Wincott, F. E., Caruthers, M. H., *J. Am. Chem. Soc.*, 120: 11820-11821, 1998; triisopropylsilyloxy methyl (TOM), Pitsch, S., Weiss, P. A., Jenny, L., Stutz, A., Wu, X., *Helv. Chim. Acta.* 84, 3773-3795, 2001; and, t-butyldithiomethyl (DTM) (compound 7), Semenyuk, A., Foldesi, A., Johansson, T., Estmer-Nilsson, C., Blomgren, P., Brannvall, M., Kirsebom, L. A., Kwiatkowski, M., *J. Am. Chem. Soc.*, 128: 12356-12357, 2006. Any of these compounds can be utilized in conjunction with the 3'-terminal silyl ether to produce RNA or DNA's of the present invention.

Various ligands and chromophores can conveniently and efficiently be introduced within the sequence of RNA molecules or DNA molecules, which contain terminal cyclic phosphate.

Similarly chemically modified RNA or DNA can be introduced in the oligonucleotide chain having terminal cyclic phosphate. Thus modified arabino sugars, 2'-deoxy-2'-fluoro-beta-D_arabinonucleic acid (FANA; compound 8)) and 2'-deoxy-4'-thio-2'-fluoro-beta-D_arabinonucleic acid (4'-Thio-FANA; compound 9) can be introduced into sequences for SiRNA activities, Dowler, T., Bergeron, D., Tedeschi, Anna-Lisa, Paquet, L., Ferrari, N., Damha, M. J., *Nucl. Acids Res.*, 34, 1669-1675, 2006.

Those modified nucleotides have become among the most important modifications in drug candidates, substantially improving nuclease resistance and chemical stability of the desired oligonucleotides.

Amongst the several new 2'-protecting groups that have been developed, the 2'-protecting 2-cyanoethoxymethyl (CEM) (compound 10) has been shown to produce very long RNA. This strategy can be utilized to synthesize oligonucleotides of long chain, i.e., the sequences joining the terminal phosphate containing nucleoside attached to our solid support designed to produce terminal cyclic phosphate. However, the quality of RNA produced by CEM technology remains in question at this time.

(compound 7)

(2'-DTM-RNA amidites)

(compound 8)

2'-F-ANA modified phosphoramidites
phosphoramidites (compound 9)

4'-Thio-2'-F-ANA modified (compound 10)

2'-CEM Protected RNA Intermediates

Chemical synthesis of RNA and DNA with terminal cyclic phosphate is desirable because it avoids the inefficiencies and limitation of scale of synthesis; such as by in vitro transcription by T7 RNA polymerase, Helm, M., Brule, H., Giege, R., Florence, C., *RNA*, 5:618-621, 1999. Chemical synthesis of RNA as such is also desirable for studies of RNA structure and function, and many useful modifications can be achieved selectively, such as site specific introduction of functional groups; viz., disulfphide cross linking as a probe of RNA tertiary structures, Maglott, E. J., Glick, G. D., *Nucl. Acids Res.*, 26: 1301-1308, 1999. The synthesis of long RNA is very important for biologically active molecules such as tRNA, and such synthesis have been achieved, Persson, T., Kutzke, U., Busch, S., Held, R., Harmann, R. K., *Bioorgan. Med. Chem.*, 9:51-56, 2001; Oglvie, K. K., Usman, N., Nicoghosian, K., Cedrgren, R. J., *Proc. Natl. Acad. Sci.*, USA, 85:5764-5768, 1988; Bratty, J., Wu, T., Nicoghosian, K., Ogilvie, K. K., Perreault, J.-P., Keith, G., Cedergren, R. J., *F.E.B.S. Lett.*, 269:60-64 , 1990; Gasparutto, D., Livache, T., Bazin, H., Duplaa, A. M., Guy, A., Khorlin, A., Molko, D., Roget, A., Teoule, R., *Nucl. Acids. Res.*, 20:5159-5166, 1992; Goodwin, J. T., Stanick, W. A., Glick, G. D., *J. Org. Chem.*, 59:7941-7943, 1994.

With the introduction of terminal cyclic phosphate, such biologically significant DNA and RNA will be realizable, and will be available to study roles of such DNA and RNA.

No efficient techniques to make DNA and RNA possessing cyclic phosphates is presently available, including the technique described by, Joseph S. Vyle, Nicholas H. Williams, Jane A. Grasby, *Tetrahedron Let.*, 39,7975-7978,1998. But with our method, we have observed high coupling efficiency per step during automated oligo synthesis with the solid support, which eventually allows formation of cyclic phosphate of this invention. The process is capable of producing very long DNA and RNA oligonucleotides.

The t-butyldimethylsilyl protecting group on 2'-hydroxyl of ribonucleosides has been the group of choice for making 3'-phosphoramidites and utilizing them for oligonucleotide synthesis. It has been shown to migrate to 3'-hydroxyl position rather easily. This has been documented amply and in detail (Ogilvie, K. K., and Entwistle, D. W. *Carbohydrate Res.*, 89, 203-210, 1981; Wu, T., and Ogilvie, K. K. *J. Org. Chem.*, 55, 4717-4734, 1990). We have utilized this protecting group to produce cyclic phosphates of our invention.

The present invention is directed towards the synthesis of high purity DNA and RNA's, specifically to introduce cyclic phosphate at 3'-end of oligonucleotides of synthetic RNA's. Such DNA and RNA's have vast application in therapeutics, diagnostics, drug design, and selective inhibition of an RNA sequence within cellular environment; blocking a function of different types of RNA molecules present inside of the cell. Silencing gene expression at mRNA level with nucleic acid based molecules is a fascinating new approach. Among these, RNA interference (RNAi) has emerged as a proven approach that offers great potential for selective gene inhibition and shows great promise for application in control and management of various biochemical and pharmacological processes. Early studies by Fire et al., reported in Fire, A., Xu, S., Montgomery, M. K., Kostas, S. A., Driver, S. E., and Mello, C. C, *Nature*, 391, 806-811, 1998, showed that RNA interference in Caenorhabditiselegans is mediated by 21 and 22 nucleotide RNA sequences. This was further confirmed as general phenomenon of specific inhibition of gene expression by small double stranded RNA's being mediated by 21 and 22 nucleotide RNA's, *Genes Dev.*, 15, 188-200, 2001. Simultaneous studies by Capie, N. J., Parrish, S., Imani, F., Fire, A., and Morgan , R. A., confirmed such phenomenon of specific gene expression by small double stranded (dSds) RNAs in invertebrates and vertebrates alike. Subsequently, a vast amount of research led to confirmation of above studies and established RNAi as a powerful tool for selectively and very specific gene inhibition and regulation, Nishikura, K., *Cell*, 107, 415-418, 2001; Nykanen, A., Haley, B., Zamore, P. D., *Cell*, 107, 309-321, 2001; Tuschl, T., *Nat. Biotechnol.*, 20, 446-448, 2002; Mittal, V., *Nature Rev.*, 5, 355-365, 2004; *Proc. Natl. Acad. Sci. USA*, 99, 6047-6052, 2002; Donze, O. & Picard, D., *Nucl. Acids. Res.*, 30, e46,2002; Sui, G., Soohoo, C., Affar el, B., Gay, F., Shi,Y., Forrester, W. C., and Shi, Y., *Proc. Natl. Acad. Sci. USA*, 99, 5515-5520, 2002; Paddison, P. J., Caudy, A. A., Bernstein, E., Hannon, G. J., and Conklin, D. S., *Genes Dev.*, 16, 948-959, 2002.

Our invention would further allow the synthesis of defined sequence DNA and RNA having various lipophilic or hydrophobic groups in synthetic DNA and RNA having terminal cyclic phosphate group. Thus siRNA can be synthesized with terminal cyclic phosphate, thus enhancing such modified siRNA; the delivery and optimization of targets can be addressed and desired biological results can be achieved through bioconjugation. This approach allows for the attachment to be done at any internal position of an oligonucleotide chain, even at the terminal nucleoside itself, without causing any loss of chemical activity during cyclic phosphate formation. The design of nuclease resistant siRNA has been the subject of intense research and development recently in order to develop effective therapeutics. Thus base modifications such as, 2-thiouridine, pseudouridine, dihydrouridine have revealed the effect on conformations of RNA molecules and the associated biological activity; Sipa, K., Sochacka, E., Kazmierczak-Baranska, J., Maszewska, M., Janicka, M., Nowak, G., Nawrot, B., RNA, 13, 1301-1316, 2007. It was shown that 2'-modified RNA's, especially 2'-fluoro, have great resistance towards nuclease and are biologically active in vivo, Layzer, J. M., McCaffrey, A. P., Tanner, A. K., Huang, Z., Kay, M. A., and Sullenger, B. A., RNA, 10, 766-771, 2004. Also studied are the 2'-O-Alkyl-modifications, such as 2'-Omethyl's and 2'-O-MOE, Prakash, S., Allerson, C V. R., Dande, P., Vickers, T. A., Siofi, T. A., Jarres, R., Baker, B. F., Swayze, E. E., Griffey, R. H., and Bhat, B., J. Med. Chem., 48, 4247, 4253, 2005. The same authors used 4'-thio modified sugar nucleosides in combination of 2'-O alkyl modification for improving SiRNA siRNA properties and RNAi enhancement, Dande, P., Prakas, T. P., Sioufi, N., Gaus, H., Jarres, R., Berdeja, A., Swayne, E. E., Griffey, R. H., Bhat, B. K, J. Med. Chem., 49, 1624-1634, 2006. The replacement of internucleotide phosphate with phosphorothioate and boranophosphates of sSiRNAs have shown promise in vivo, Li, Z. Y., Mao, H., Kallick, D. A., and Gorenstein, D. G., Biochem. Biophys. Res. Comm., 329, 1026-1030, 2005; and, Hall, A. H. S., Wan, J., Shaughnessy, E. E., Ramsay Shaw, B., Alexander, K. A., Nucl. Acids Res., 32, 5991-6000, 2004. Such modifications are conceivable at any base within an oligonucleotide. Similarly 2'-5'-linked DNA and RNA have been developed in the past. These RNA activate latent endo-ribonucleaseRNase L, which subsequently cleaves the messenger and ribosomal RNAs, R. Charubala, E. Uhlmann, F. Himmelsbach, W. Pfleiderer, Helv. Chim. Acta., 70, 2028,1987; M. Wasner, D. Arion G. Borkow, A. Noronha, A. Uddin, M. Parniak, M. Damha, Biochemistry, 37, 7478-7486,1998. Such RNA's possessing a terminal cyclic phosphate present an opportunity to investigate detailed mechanistic understanding of the biological processes and to develop potential diagnostic and therapeutic molecules.

Bioconjugation of siRNA molecules, biologically active RNA molecules, aptamers, and synthetic DMNA molecules requires a key feature for cell membrane permeability, in addition to in vivo stability and of appropriate modification of nucleosides: insufficient cross-membrane cellular uptake limits the utility of sSi RNA's, other single stranded RNA's, or even various DNA molecules. Thus cholesterol attached at 3'-end of sSiRNA, has been shown to improve in-vivo cell trafficking and therapeutic silencing of gene, Soutschek, J., Akine, A., Bramlage, B., Charisse, K., Constein, R., Donoghue, M., Elbasir, S., Geickk, A., Hadwiger, P., Harborth, J., Nature, 432, 173-0178, 2004. Having such modified oligonucleotides with terminal cyclic phosphates offers new horizons in biological research and development.

Among various conjugations, (besides cholesterol), which have been developed, areas follow:

(a) Natural and synthetic protein transduction domains (PTDs), also called cell permeating peptides (CPPs) or membrane permeant peptides (MPPs), which are short amino acid sequences that are able to interact with the plasma membrane. The uptake of MPP-sSiRNA conjugates takes place rapidly. Such peptides can be conjugated preferably to the 3'- of stand strand.

(b) Other polycationic molecules can be conjugated at the 3'-end of either sense or antisense strand of RNA.

(c) PEG (polyethylene glycols-oligonucleotide conjugates) have been used in various complex processes for significant gene silencing effect after uptake into the target cells, Oishi, M., Nagasaki, Y., Itaka, K., Nishiyama, N., and Kataoka, K., J. Am. Chem. Soc., 127, 1624-1625, 2005.

(d) Aptamers have been used for site specific delivery of sSiRNA's. Since aptamers have high affinity for their targets, the conjugates with sSiRNA act as excellent delivery systems, which result in efficient inhibition of the target gene expression, Chu, T. C., Twu, K. Y., Ellington, A. D. and Levy, M., Nucl. Acids Res., 4(10), e73, 2006. These molecules can once again be conjugated at the 3'-end of siRNA or other biologically active oligonucleotides.

(e) Various lipid conjugations at the 3'-end can be achieved through our invention and can be utilized for efficient internalization of oligonucleotides. The lipophilic moiety can consist of a hydroxyl function to synthesize a phopsphoramidite. Similarly, the lipophilic moiety can have carboxylic function at the terminus. The later can be coupled to a 3'-amino group having a spacer, synthesized by last addition of amino linkers, such as C-6 amino linker amidite, of the reverse synthesized oligonucleotide, to the carboxylic moiety using DCC (dicyclohexylcabodiimide) or similar coupling reagent.

These research papers have been reviewed elegantly by Paula, De. D., Bentley, M. V. L. B., Mahao, R. L., RNA, 13, 431-456, 2007. Cyclic phosphates of many DNA and RNA have been implicated in various biochemical pathways.

Another class of RNA, closely related to siRNA, is microRNA, (commonly referred to as miRNA). These is a large class of non coding RNA's which have a significant role in gene regulation, Bartel, D. P. Cell, 116,281-297, 2004; He, L., Hannon, G. J. Nat. Rev. Genet, 5:522-531, 2004; Lagos-Quintana, M., Rauhut, R., Lendeckel, W., Tuschl, T., Science, 204:853-858,2001. In the human genome there are at least 1000 miRNA scattered across the entire genome. A number of these micro RNA's down regulate large numbers of target mRNAs, Lim, L. P., Lau, N. C., Garrett-Engele, P., Grimson, A., Schelter, J. M., Castle, J., Bartel, D. P., Linsey, P. S., Johnson, J. M., Nature, 433:769-773, 2005. Different combinations of miRNAs are possibly involved in regulation of target gene in mammalian cell. It has also been shown that siRNA can function as miRNAs, Krek, A., Grun, D., Poy, M. N., Wolf, R., Rosenberg, L., Epstein, E. J., MacMenamin, P., da Piedade, I., Gunsalus, K. C., Stoffel, M., Nat. Genet., 37: 495-500, 2005; Doench, J. G., Petersen, C. P., Sharp, P. A., Genes Dev., 17:438-442, 2003. The miRNA's molecules have a great potential in therapeutics and in gene regulation, Hammond, S. M., Trends Mol. Med. 12:99-101, 2006. A vast amount of efforts is currently devoted towards understanding miRNA pathways, their role in development and diseases, specially focusing on cancer; miRNA targets are being developed for therapeutic and diagnostics development. A great number of miRNA is being identified and their role is being determined through microarrays, PCR, and informatics. Synthesis of RNA designed to target miRNA also requires RNA synthesis and modification similar to those required for sSiRNA's for stability of RNA and bioconjugation for better cellular uptake. Terminal cyclic phosphate terminated oligonucleotides are expected to play important roles in various processes in such RNA's.

SUMMARY OF THE INVENTION

The invention provides a novel method for the synthesis of 2',3'-cyclic phosphate and phosphorothioate of mono and terminated oligonucleotides synthesis and synthesis of 2',3'- and 3',5'-cyclic phosphate nucleosides. This method can be used for the introduction of 2',3-cyclic phosphate and phosphorothioate modification into RNA and various RNA chimeric molecules. This invention provides solid support compositions suitable for the synthesis of 2',3'-cyclic phosphate and phosphorothioate of mono and terminated oligonucleotides synthesis, and can be made available in kits with at least one solid support composition. The invention also provides solid support compositions suitable for the synthesis of 2',3'- and 3',5'-cyclic phosphate and phosphorothioate of mononucleotide and nucleotide synthesis, and can be made available in kits with at least one solid support composition.

With the present invention, it is possible to synthesize various classes of defined sequence RNA molecules in the 3', 5' direction, and use them for the synthesis and development of a variety of therapeutic grade RNA aptamers, tRNA's, siRNA, and biologically active RNA molecules.

The oligoribo nucleotide and oligodeoxyribonucleotide molecules can both be synthesized using the solid support of the present invention. Subsequent to synthesis on the support, the base protecting groups on the oligodeoxy nucleotide or oligoribonucleotide can be deprotected safely while the solid support is still bound with the latent cyclic phosphate moiety at the terminal. The invention is directed towards the synthesis of high purity DNA and RNA's specifically to introduce cyclic phosphate at 3'-end of oligonucleotides of synthetic RNA's. Such DNA and RNA's have vast application in therapeutics, diagnostics, drug design, and selective inhibition of an RNA sequence within cellular environment, blocking a function of different types of RNA present inside cell.

DETAILED DESCRIPTION OF THE INVENTION

The invention provides a method for the synthesis of 2',3'-cyclic phosphate mono and terminated oligonucleotides synthesis and 2',3'-cyclic phosphate nucleosides using solid support that has a phosphoramidate linker (Formula 1). The hydroxyl group in the neighboring 2'-position is protected with the group that has to be intact, and can be removed only after oligonucleotide base deprotection step under basic conditions. Subsequent removal of 2'-hydroxyl protecting group leads to simultaneous formation of 2',3-cyclic phosphate in orthogonal conditions.

Formula 1

Where B = a) U, b) A (N—Bz), c) C (N—Ac), d) G (N-iBu).

The present invention also provides solid support suitable for the synthesis of 2',3'-cyclic phosphorothioate mono and oligonucleotides. (Formula 2)

(Formula 2)

Where B = a) U, b) A (N—Bz), c) C (N—Ac), d) G (N-iBu).

In one embodiment, oligonucleotide is elongated and base protecting groups removed on solid support, when 2'-protecting group remains intact. Removal of 2'-protecting group in neutral or mild acidic conditions generates cyclic phosphate (Scheme 1).

Scheme 1

Where B = a) U, b) A (N—Bz), c) C (N—Ac), d) G (N—iBu).

In another embodiment, oligonucleotide is elongated and then cleaved from the solid support into solution phase followed by base deprotection. The protecting group at 2' position remains intact until it is cleaved and 2'-hydroxyl is available to form cyclic phosphate (Scheme 2).

Figure 1:
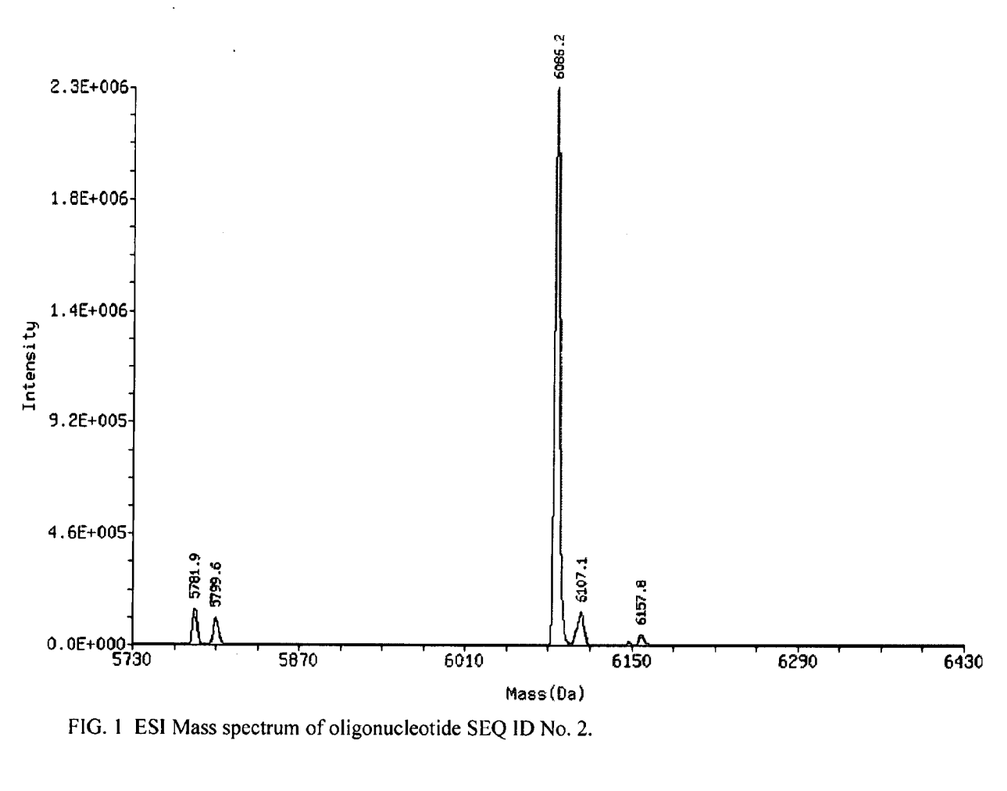
FIG. 1. ESI Mass spectrum of oligonucleotide SEQ ID No. 2.
Figure 2:
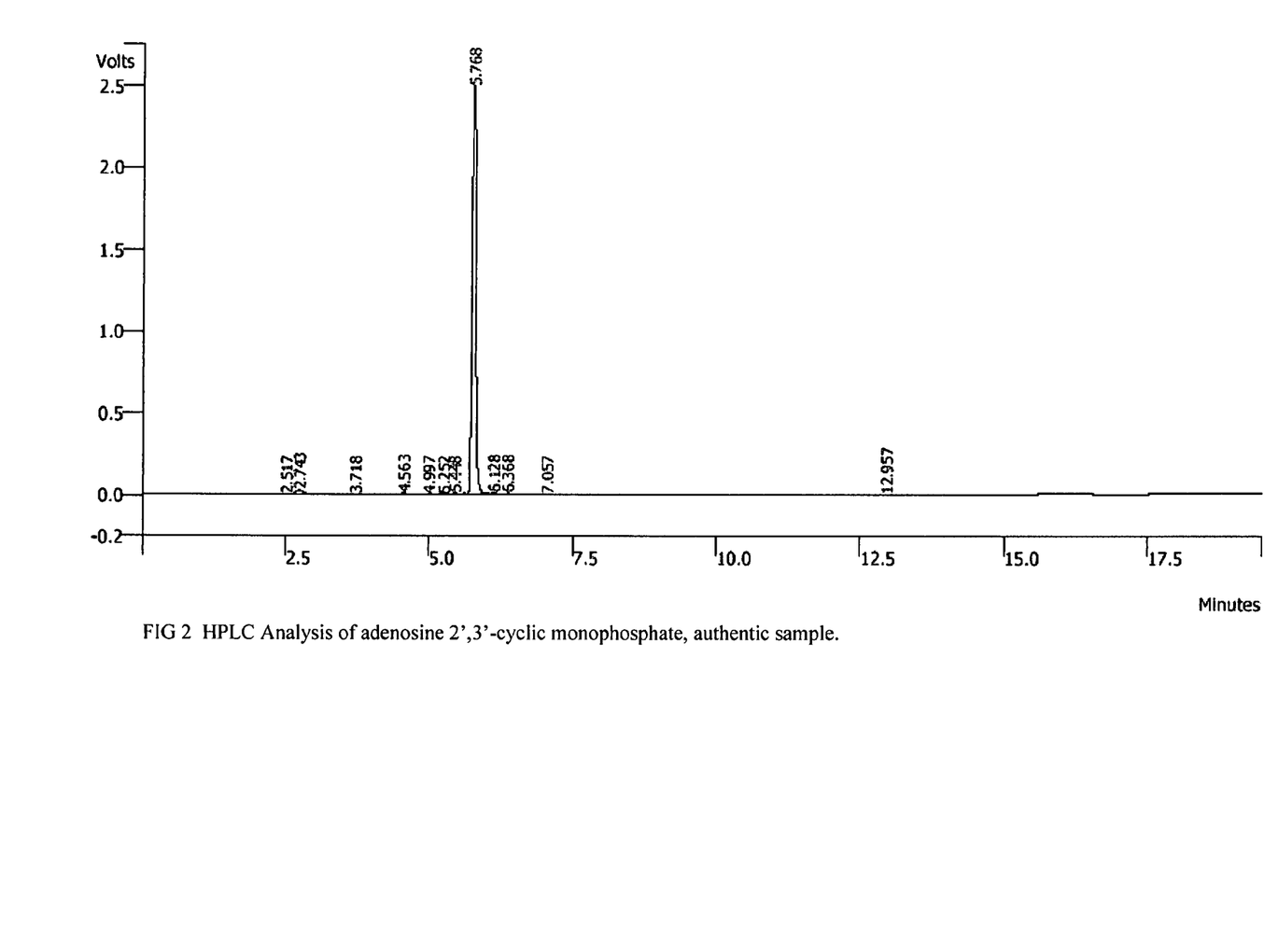
FIG. 2. HPLC Analysis of adenosine 2',3'-cyclic monophosphate, authentic sample.
Figure 3:
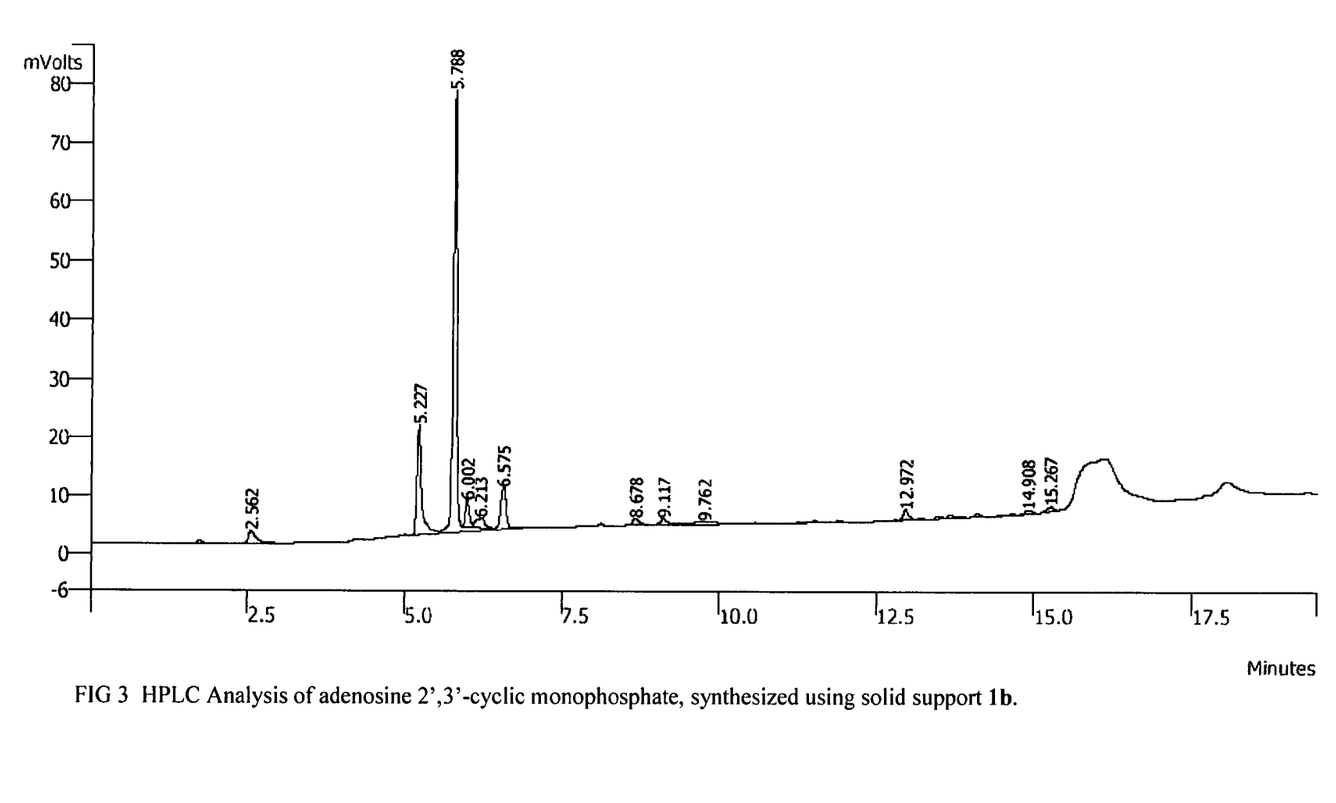
FIG. 3. HPLC Analysis of adenosine 2',3'-cyclic monophosphate, synthesized using solid support 1b.
Figure 4:
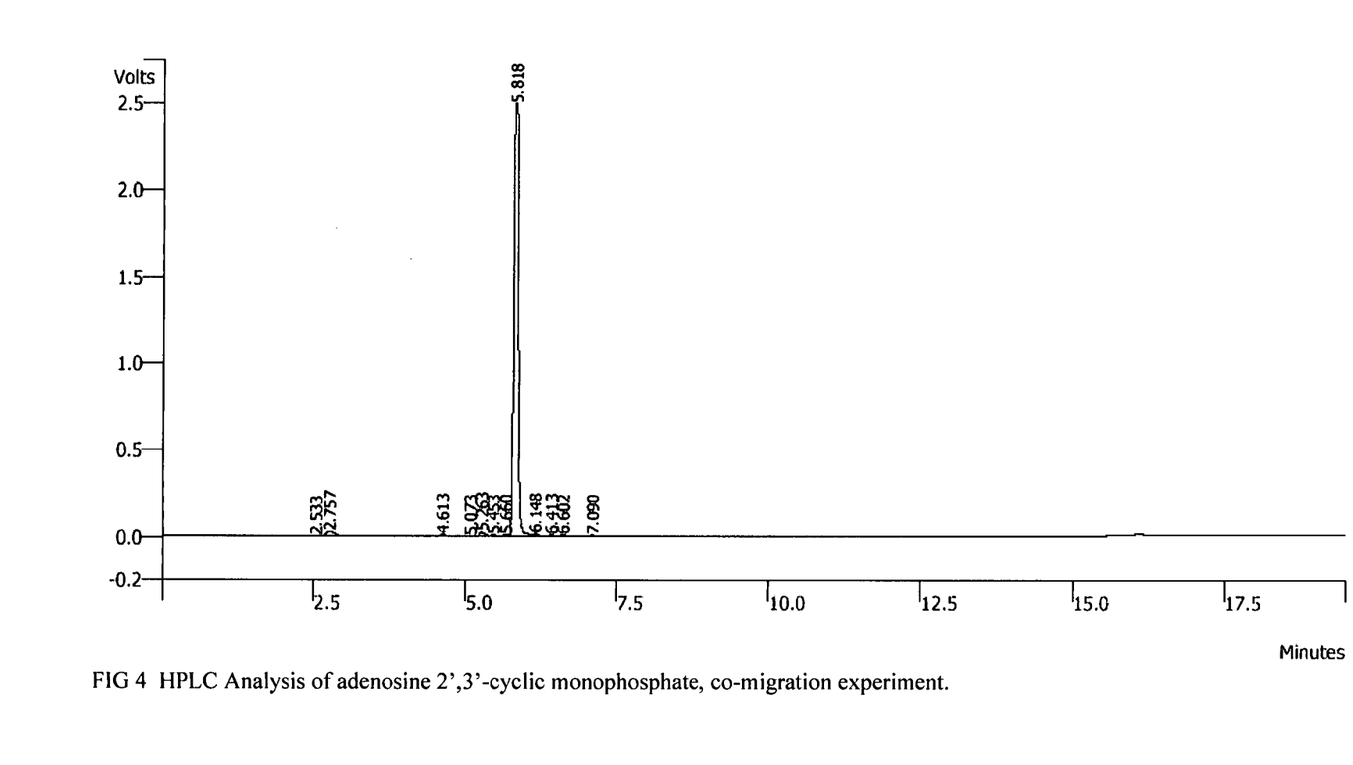
FIG. 4. HPLC Analysis of adenosine 2',3'-cyclic monophosphate, co-migration experiment.

In another embodiment, the 3'-terminal nucleotide has 2'-phosphoramidateate linker and protecting group at 3' position of the ribose (FIG. 3). When oligonucleotide is cleaved and nuclear bases deprotected, the removal of 3'-hydroxyl protecting group results in the same 2',3'-cyclic phosphate formation (Scheme 3).

(Formula 3)

Where B = a) U, b) A (N—Bz), c) C (N—Ac), d) G (N-iBu).

Scheme 3

Where B = a) U, b) A (N—Bz), c) C (N—Ac), d) G (N—iBu).

The present invention also provides solid support suitable for the synthesis of 5',3'-cyclic phosphate mononucleotides. (Scheme 4)

Scheme 4

-continued

Where B = a) U, b) A (N—Bz), c) C (N—Ac), d) G (N—iBu).

EXPERIMENTAL: EXAMPLES

Example 1

Synthesis of 2'-O-TBDMS-5'-O-DMT-uridine-3'-cyanoethyl-phosphoramidyl-CPG 1a. MMT-Amino C-6 phosphoramidite was coupled to 3'-phosphateCPG using Applied Biosystems Model Expedite 8900 DNA/RNA synthesizer in 15 ſ mole scale. The terminal monomethoxytrityl group was removed manually followed by coupling of 2'-O-TBDMS-5'-O-DMT-uridine-3'-cyanoethyl-phosphoramidite using standard 15 ſ mole RNA coupling cycle, affording desired 2'-O-TBDMS-5'-O-DMT-uridine-3'-cyanoethyl-phosphoramidyl-CPG 1a with final loading 25-30 ſ mole/g.

Synthesis of N$^4$-benzoyl-2'O-TBDMS-5'-O-DMT-adenosine-3'-cyanoethyl-phosphoramidyl-CPG 1b. N$^4$-Benzoyl-2'O-TBDMS-5'-O-DMT-adenosine-3'-cyanoethyl-phosphoramidyl-CPG 1b was prepared analogously to 2'-O-TBDMS-5'-O-DMT-uridine-3'-cyanoethyl-phosphoramidyl-CPG 1a with final loading 25-30 ſ mole/g.

Synthesis of N$^2$-isobutyryl-2'O-TBDMS-5'-O-DMT-guanosine-3'-cyanoethyl-phosphoramidyl-CPG 1d. N$^2$-Isobutyryl-2'O-TBDMS-5'-O-DMT-guanosine-3'-cyanoethyl-phosphoramidyl-CPG 1d was prepared analogously to 2'-O-TBDMS-5'-O-DMT-uridine-3'-cyanoethyl-phosphoramidyl-CPG 1a with final loading 20-25 ſ mole/g.

Synthesis of 2'-O-TBDMS-5'-O-DMT-uridine-3'-cyanoethyl-phosphoramidyl-CPG 3 (non-cleavable). 2'-O-TBDMS-5'-O-DMT-uridine-3'-cyanoethyl-phosphoramidite was coupled to amino-1caa-CPG using 15 ſ mole RNA coupling cycle affording desired 2'-O-TBDMS-5'-O-DMT-uridine-3'-cyanoethyl-phosphoramidyl-CPG 3 with final loading 35-40 ſ mole/g.

Example 2

Synthesis of adenosine 2',3'-cyclic monophosphate. To 10 mg of N$^4$-benzoyl-2'O-TBDMS-5'-O-DMT-adenosine-3'-cyanoethyl-phosphoramidyl-CPG 1b was added 0.5 mL of concentrated aqueous solution of methylamine (40%). After 1 hr the reaction mixture was filtered and the filtrate was placed in 2 mL screw cap centrifuge vial at 50° C. After 1 hr the solvent was removed under diminished pressure to dryness and 50 ſ L of TEA/3HF solution was added to the resulting residue. After 1 hr 500 ſ L of 2% LiClO$_4$ in acetone were added to the reaction mixture. The precipitant was centrifuged and supernatant solution was removed. The final adenosine 2',3'-cyclic monophosphate was washed with acetone and dried under diminished pressure. The identity of the adenosine 2',3'-cyclic monophosphate was confirmed by analytical RP HPLC by co-migration experiment: column—ChromSep SS (4.6×250), eluent A—0.1 M TEAA (pH 7.5), eluent B—acetonitrile, gradient—5 to 60% eluent B during 20 min at flow rate 1.0 mL/min. The retention time of adenosine 2',3'-cyclic monophosphate under these conditions is 5.78 min.

Example 3

Oligonucleotide Synthesis: The following oligonucleotides (Table 1) were synthesized using 3' 5' directed standard phosphoramidite chemistry in 1 ʃ mole scale. The syntheses were performed on Expedite 8900 synthesizer using standard DNA or RNA 1 ʃ mole cycles. Following synthesis, the controlled pore glass (CPG) solid support was transferred to a 2 ml microfuge tube. Oligonucleotides were cleaved from the CPG and deprotected by incubation for 30 min at 65° C. in 1 ml of 40% methylamine solution in water. The supernatant was removed and the CPG was washed with 1 ml of water; supernatants were pooled and dried. The t-butyl-dimethylsilyl protecting group was removed and 2',3'-cyclic phosphate was formed by treatment with 150 ʃ l of fresh anhydrous triethylammonium-trihydrogen fluoride at room temperature in ultrasonic bath for 1 hour. The oligonucleotide was precipitated by 1.5 ml of n-butanol; the sample was cooled at −70° C. for 1 hour then centrifuged at 10,000 g for 10 minutes. The supernatant was decanted and the pellet was washed with n-butanol one more time.

TABLE 1

| 2'-3'-Cyclic phosphate oligonucleotide sequences. |  |
|---|---|
| SEQ ID No. 1 | TTTTTTTTTrUcP |
| SEQ ID No. 2 | TTTTTTTTTTTTTTTTTTTrUcP |
| SEQ ID No. 3 | mAmCmUmUmGmUmUmGmAmCmArUrUcP |
| SEQ ID No. 4 | TTTTTTTTTTTTTTTTTTTrGcP |

Crude oligonucleotides were analyzed by CE and the identities of the oligonucleotides SEQ ID No.1-4 were confirmed by ESI mass-spectrometry.

We claim:

1. A nucleotide having the formula 4,

Formula 4 wherein,

B is a nucleoside base radical selected from the group consisting of 9-($N^6$-benzoyladeninyl)-, 9-($N^6$-(N,N-dimethylformamidinyl)-adeninyl)-, 1-($N^4$-acetylcytosinyl)-, 1-($N^4$-benzoylcytosinyl)-, 1-($N^4$-isobutyrylcytosinyl)-, 1-($N^4$-(N,N-dimethylformamidinyl)-cytosinyl)-, 1-($N^4$-phenoxyacetylcytosinyl)-, 1-($N^4$-tert-butylphenoxyacetylcytosinyl)-, 1-($N^4$-isopropyl phenoxyacetylcytosinyl)-, 9-($N^2$-isobutyrylguaninyl)-, 9-($N^2$-tert-butylphenoxyacetylguaninyl)-, 9-($N^2$-isopropylphenoxyacetylguaninyl)-, 9-($N^6$-(N,N-dimethylformamidinyl)-guaninyl)-, and 1-uracilyl-;

or, a modified nucleoside base radical selected from the group consisting of 9-hypoxanthinyl, 1-thyminyl, 9-purinyl, 9-($N^2$-phenoxyacetyl-2-aminopurinyl) 9-($N^{2'}N^6$-diphenoxyacetyl-2,6-diaminopurinyl)-, pseudouracilyl, 5-fluoro-1-uracilyl-, 1-($N^4$-benzoyl-5-fluorocytosinyl)-, 5-methyl-1-uracilyl-, 1-($N^4$-benzoyl-5-methylcytosinyl)-, 5-bromo-1-uracilyl-, 1-($N^4$-benzoyl-5-bromocytosinyl)-, 5-iodo-1-uracilyl, 5-vinyl-1-uracilyl, $N^3$-methyl-1-uracilyl-, 5-vinyl-1-uracilyl-, 1-($N^4$-benzoyl-$N^3$-methylcytosinyl)-, $N^3$-methyl-1-thyminyl-, 4-thio-1-uracilyl-, 9-($N^6$-benzoyl-8-bromoadeninyl)-, 9-($N^6$-benzoyl-8-oxoadeninyl)-9-($N^2$-isobutyryl-8-oxoguaninyl)-, 9-($N^6$-(N,N-dimethylformamidinyl)-8-oxoguaninyl)-, 8-oxo-9-hypoxanthinyl, 8-bromo-9-hypoxanthinyl-, 9-($N^1$-methyl-$N^6$-(9-fluorenylmethyloxycarbonyl)-adeninyl)-, $N^1$-methyl-9-hypoxanthinyl-, 9-($N^1$-methyl-$N^2$-(9-fluorenylmethyloxycarbonyl)-guaninyl)-, etheno-9-adeninyl-, and etheno-1-cytosinyl-;

Y is an oxygen atom or sulfur atom;

X is a linker chain of between $C_{1-100}$, selected from the group consisting of alkyl, alkenyl, cycloalkyl, aryl, and aralkyl in a hydrocarbyl diradical moiety, optionally incorporating the intervening groups —O—, —S—, —S(O)$_2$—, —C(O)—, or —NR$_4$—, where R$_4$ is a hydrogen radical, or a substituted $C_1$ to $C_{20}$ alkyl or a substituted aralkyl, and connected to a solid support suitable for oligonucleotide synthesis;

W is a linker that contains an ester bond or an oxyethylsulfone group;

Z is controlled pore glass (CPG) or polystyrene;

R$_1$ is a protecting group selected from the group consisting of a dimethoxytrityl group (DMT), and a monomethoxytrityl group (MMT), or a hydrogen radical, or an oligonucleotide chain;

R$_2$ is tert-butyl-dimethylsilyl group (TBDMS), triisopropylsilyl oxymethylene group (TOM), 1-(2-fluorophenyl)-4-methoxypiperidiny-4-yl group (Fpmp), 1-(4-chlorophenyl)-4-methoxypiperidiny-4-yl group (CPEP), tetrahydropyranyl group (THP) or O-bis(2-acetoxyethoxy)methyl group (ACE); and R$_3$ is a cyanoethyl, methyl, ethyl or benzyl radical.

2. The compound of claim 1 wherein B is a radical of formula 5,

Formula 5 wherein,

Y is a member of the group consisting of propenyl, propynyl, a hydrocarbyl chain with 2-20 carbon atoms, optionally substituted by one or more heteroatoms independently selected from the group consisting of oxygen, sulfur, and —(NH)—; and Z is a moiety selected from the group consisting of fluorophores, quenchers, biotin, and cholesterol.

3. The compound of claim 1 wherein B is a radical of formula 6,

Formula 6 wherein,
Y is a member of the group consisting of propenyl, propynyl, a hydrocarbyl chain with 2-20 carbon atoms, wherein the hydrocarbyl chain may optionally include in the chain one or more heteroatom-derived groups independently selected from the group consisting of oxygen, sulfur, and —(NH)—;
Z is a moiety selected from the group consisting of fluorophores, quenchers, biotin, cholesterol; and,
R is an amine protecting group selected from the group consisting of acetyl, benzoyl, phenoxyacetyl, tert-butylphenoxyacetyl, dimethylformamidinyl, and dibutylformamidinyl.

4. The compound of claim 1 wherein B is a radical of formula 7,

Formula 7 wherein,
X is oxygen, sulfur or nitrogen;
Y is a member of the group consisting of propenyl, propynyl, a hydrocarbyl chain with 2-20 carbon atoms, wherein the hydrocarbyl chain may optionally include in the chain one or more heteroatom-derived groups independently selected from the group consisting of oxygen, sulfur, and —(NH)—;
Z is a moiety selected from the group consisting of fluorophores, quenchers, biotin, cholesterol; and,
R is an amine protecting group selected from the group consisting of acetyl, benzoyl, phenoxyacetyl, tert-butylphenoxyacetyl, dimethylformamidinyl, and dibutylformamidinyl.

5. The compound of claim 1 wherein B is a radical of formula 8,

Formula 8 wherein,
X is oxygen, sulfur or nitrogen;
Y is a member of the group consisting of propenyl, propynyl, a hydrocarbyl chain of 2-20 carbon atoms wherein the hydrocarbyl chain may optionally include in the chain one or more heteroatom-derived groups independently selected from the group consisting of oxygen, sulfur, and —(NH)—;
Z is a moiety selected from the group consisting of fluorophores, quenchers, biotin, cholesterol; and,
R is an amine protecting group selected from the group consisting of acetyl, benzoyl, phenoxyacetyl, tert-butylphenoxyacetyl, dimethylformamidinyl, and dibutylformamidinyl.

6. A nucleotide having the formula 10,

Formula 10 wherein,
B is a nucleoside base radical selected from the group consisting of 9-($N^6$-benzoyladeninyl)-, 9-($N^6$-(N,N-dimethylformamidinyl)-adeninyl)-, 1-($N^4$-acetylcytosinyl)-, 1-($N^4$-benzoylcytosinyl)-, 1-($N^4$-isobutyrylcytosinyl)-, 1-($N^4$-(N,N-dimethylformamidinyl)-cytosinyl)-, 1-($N^4$-phenoxyacetylcytosinyl)-, 1-($N^4$-tert-butylphenoxyacetylcytosinyl)-, 1-($N^4$-isopropyl phenoxyacetylcytosinyl)-, 9-($N^2$-isobutyrylguaninyl)-, 9-($N^2$-tert-butylphenoxyacetylguaninyl)-, 9-($N^2$-isopropylphenoxyacetylguaninyl)-, 9-($N^6$-(N,N-dimethylformamidinyl)-guaninyl)-, and 1-uracilyl-;
or, a modified nucleoside base radical selected from the group consisting of 9-hypoxanthinyl, 1-thyminyl, 9-purinyl, 9-($N^2$-phenoxyacetyl-2-aminopurinyl)- 9-($N^{2'}N^6$-diphenoxyacetyl-2,6-diarninopurinyl)-, pseudouracilyl, 5-fluoro-1-uracilyl-, 1-($N^4$-benzoyl-5-fluorocytosinyl)-, 5-methyl-1-uracilyl-, 1-($N^4$-benzoyl-5-methylcytosinyl)-, 5-bromo-1-uracilyl-, 1-($N^4$-benzoyl-5-bromocytosinyl)-, 5-iodo-1-uracilyl, 5-vinyl-1-uracilyl, $N^3$-methyl-1-uracilyl-, 5-vinyl-1-uracilyl-, 1-($N^4$-benzoyl-$N^3$-methylcytosinyl)-, $N^3$-methyl-1-thyminyl-, 4-thio-1-uracilyl-, 9-($N^6$-benzoyl-8-bromoadeninyl)-, 9-($N^6$-benzoyl-8-oxoadeninyl)-9-($N^2$-isobutyryl-8-oxoguaninyl)-, 9-($N^6$-(N,N-dimethylformamidinyl)-8-oxoguaninyl)-, 8-oxo-9-hypoxanthinyl, 8-bromo-9-hypoxanthinyl-, 9-($N^1$-methyl-$N^6$-(9-fluorenylmethyloxycarbonyl)-adeninyl)-, $N^1$-methyl-9-hypoxanthinyl-, 9-($N^1$-methyl-$N^2$-(9-fluorenylmethyloxycarbonyl)-guaninyl)-, etheno-9-adeninyl-, and etheno-1-cytosinyl-;
Y is an oxygen atom or sulfur atom;
X is a linker chain of between $C_{1-100}$, selected from the group consisting of alkyl, alkenyl, cycloalkyl, aryl, and aralkyl, in a hydrocarbyl diradical moiety, optionally incorporating the intervening groups —O—, —S—, —S(O)$_2$—, —C(O)—, or -NR$_4$—, where R$_4$ is a hydrogen radical, or a substituted $C_1$ to $C_{20}$ alkyl or a substituted aralkyl, and connected to a solid support suitable for oligonucleotide synthesis;

W is a linker that contains an ester bond or an oxyethylsulfone group;

Z is controlled pore glass (CPG) or polystyrene;

$R_1$ is a protecting group selected from the group consisting of a dimethoxytrityl group (DMT), and a monomethoxytrityl group (MMT), or a hydrogen radical, or an oligonucleotide chain;

$R_2$ is tert-butyl-dimethylsilyl group (TBDMS), triisopropylsilyl oxymethylene group (TOM), 1-(2-fluorophenyl)-4-methoxypiperidiny-4-yl group (Fpmp), 1-(4-chlorophenyl)-4-methoxypiperidiny-4-yl group (CPEP), tetrahydropyranyl group (THP) or O-bis(2-acetoxyethoxy)methyl group (ACE); and, $R_3$ is a cyanoethyl, methyl, ethyl or benzyl radical.

7. A nucleotide having the formula 12,

Formula 12 wherein,

B is a nucleoside base radical selected from the group consisting of 9-($N^6$-benzoyladeninyl)-, 9-($N^6$-(N,N-dimethylformamidinyl)-adeninyl)-, 1-($N^4$-acetylcytosinyl)-, 1-($N^4$-benzoylcytosinyl)-, 1-($N^4$-isobutyrylcytosinyl)-, 1-($N^4$-(N,N-dimethylformamidinyl)-cytosinyl)-, 1-($N^4$-phenoxyacetylcytosinyl)-, 1-($N^4$-tert-butylphenoxyacetylcytosinyl)-, 1-($N^4$-isopropyl phenoxyacetylcytosinyl)-, 9-($N^2$-isobutyrylguaninyl)-, 9-($N^2$-tert-butylphenoxyacetylguaninyl)-, 9-($N^2$-isopropylphenoxyacetylguaninyl)-, 9-($N^6$-(N,N-dimethylformamidinyl)-guaninyl)-, and 1-uracilyl-;

or, a modified nucleoside base radical selected from the group consisting of 9-hypoxanthinyl, 1-thyminyl, 9-purinyl, 9-($N^2$-phenoxyacetyl-2-aminopurinyl)- 9-($N^{2'}N^6$-diphenoxyacetyl-2,6-diarninopurinyl)-, pseudouracilyl, 5-fluoro-1-uracilyl-, 1-($N^4$-benzoyl-5-fluorocytosinyl)-, 5-methyl-1-uracilyl-, 1-($N^4$-benzoyl-5-methylcytosinyl)-, 5-bromo-1-uracilyl-, 1-($N^4$-benzoyl-5-bromocytosinyl)-, 5-iodo-1-uracilyl, 5-vinyl-1-uracilyl, $N^3$-methyl-1-uracilyl-, 5-vinyl-1-uracilyl-, 1-($N^4$-benzoyl-$N^3$-methylcytosinyl)-, $N^3$-methyl-1-thyminyl-, 4-thio-1-uracilyl-, 9-($N^6$-benzoyl-8-bromoadeninyl)-, 9-($N^6$-benzoyl-8-oxoadeninyl)-9-($N^2$-isobutyryl-8-oxoguaninyl)-, 9-($N^6$-(N,N-dimethylformamidinyl)-8-oxoguaninyl)-, 8-oxo-9-hypoxanthinyl, 8-bromo-9-hypoxanthinyl-, 9-($N^1$-methyl-$N^6$-(9-fluorenylmethyloxycarbonyl)-adeninyl)-, $N^1$-methyl-9-hypoxanthinyl-, 9-($N^1$-methyl-$N^2$-(9-fluorenylmethyloxycarbonyl)-guaninyl)-, etheno-9-adeninyl-, and etheno-1-cytosinyl-;

Y is an oxygen atom or sulfur atom;

X is a linker chain of between $C_{1-100}$, selected from the group consisting of alkyl, alkenyl, cycloalkyl, aryl, and aralkyl, in a hydrocarbyl diradical moiety, optionally incorporating the intervening groups —O—, —S—, —S(O)$_2$—, —C(O)—, or —NR$_4$—, where R$_4$ is a hydrogen radical, or a substituted $C_1$ to $C_{20}$ alkyl or a substituted aralkyl, and connected to a solid support suitable for oligonucleotide synthesis;

W is a linker that contains an ester bond or an oxyethylsulfone group;

Z is controlled pore glass (CPG) or polystyrene;

$R_1$ is a protecting group selected from the group consisting of a dimethoxytrityl group (DMT), and a monomethoxytrityl group (MMT), and or a hydrogen radical;

$R_2$ is tert-butyl-dimethylsilyl group (TBDMS), triisopropylsilyl oxymethylene group (TOM), 1-(2-fluorophenyl)-4-methoxypiperidiny-4-yl group (Fpmp), 1-(4-chlorophenyl)-4-methoxypiperidiny-4-yl group (CPEP), tetrahydropyranyl group (THP) or O-bis(2-acetoxyethoxy)methyl group (ACE);

$R_3$ is a cyanoethyl, methyl, ethyl or benzyl radical.

8. A method for the synthesis of a 2',3' cyclic phosphate of Formula 13A comprising removal of the 2' or 3' protecting group under neutral or mild acidic conditions from a nucleotide of formula 4 or formula 10, Formula 13A Formula 4

Formula 10 wherein, $B_1$ is a nucleoside base radical selected from the group consisting of 9-adeninyl-, 1-cytosinyl-, 9-guaninyl-, and 1-uracilyl or, a modified nucleoside base radical selected from the group consisting of 9-hypoxanthinyl-, 1-thyminyl-, 9-purinyl-, 2-amino-9-purinyl-, 2,6-diamino-9-purinyl-, pseudouracilyl-, 5-fluoro-1uracilyl-, 5-fluoro-1-cytosinyl-, 5-methyl-1-uracilyl-, 5-methyl-1-cytosinyl-, 5-bromo-1-uracilyl-, 5-bromo-1-cytosinyl-, 5-iodo-5-vinyl-1-uracilyl-, $N^3$-methyl-1-uracilyl-, $N^3$-methyl-1-cylosinyl-, 4-thio-1-uracilyl-, 8-bromo-9-adeninyl-, 8-oxo-9-adeninyl-, 8-oxo-9-guaninyl-, 8-oxo-9-hypoxanthinyl-, 8-bromo-9-hypoxanthinyl-, $N^1$-methyl-9-adeninyl-, $N^1$-methyl-9-hypoxanthinyl-, $N^1$-methyl-9-guaninyl-, etheno-9-adeninyl-, and etheno-1 cytosinyl-;

Y is an oxygen atom or a sulfur atom;

R is dimethoxytriphenylmethyl (DMT), and a monomethoxytriphenylmethyl (MMT), or a hydrogen radical or an oligonucleotide chain;

$R_1$ is a protecting group selected from the group consisting of dimethoxytriphenylmethyl (DMT), monomethoxytriphenylmethyl (MMT), hydrogen and an oligonucleotide chain;

B is a nucleoside base radical selected from the group consisting of 9-($N^6$-benzoyladeninyl)-, 9-($N^6$-(N,N-dimethylformamidinyl)-adeninyl)-, 1-($N^4$-acetylcytosinyl)-, 1-($N^4$-benzoylcytosinyl)-, 1-($N^4$-isobutyrylcytosinyl)-, 1-($N^4$-(N,N-dimethylformamidinyl)-cytosinyl)-, 1-($N^4$-phenoxyacetylcytosinyl)-, 1-($N^4$-tert-butylphenoxyacetylcytosinyl)-, 1-($N^4$-isopropyl phenoxyacetylcytosinyl)-, 9-($N^2$-isobutyrylguaninyl)-, 9-($N^2$-tert-butylphenoxyacetylguaninyl)-, 9-($N^2$-isopropylphenoxyacetylguaninyl)-, 9-($N^6$-(N,N-dimethylformamidinyl)-guaninyl)-, and 1-uracilyl-;

or, a modified nucleoside base radical selected from the group consisting of 9-hypoxanthinyl, 1-thyminyl, 9-purinyl, 9-($N^2$-phenoxyacetyl-2-aminopurinyl)- 9-($N^{2'}N^6$-diphenoxyacetyl-2,6-diarninopurinyl)-, pseudouracilyl, 5-fluoro-1-uracilyl-, 1-($N^4$-benzoyl-5-fluorocytosinyl)-, 5-methyl-1-uracilyl-, 1-($N^4$-benzoyl-5-methylcytosinyl)-, 5-bromo-1-uracilyl-, 1-($N^4$-benzoyl-5-bromocytosinyl)-, 5-iodo-1-uracilyl, 5-vinyl-1-uracilyl, $N^3$-methyl-1-uracilyl-, 5-vinyl-1-uracilyl-, 1-($N^4$-benzoyl-$N^3$-methylcytosinyl)-, $N^3$-methyl-1-thyminyl-, 4-thio-1-uracilyl-, 9-($N^6$-benzoyl-8-bromoadeninyl)-, 9-($N^6$-benzoyl-8-oxoadeninyl)-9-($N^2$-isobutyryl-8-oxoguaninyl)-, 9-($N^6$-(N,N-dimethylformamidinyl)-8-oxoguaninyl)-, 8-oxo-9-hypoxanthinyl, 8-bromo-9-hypoxanthinyl-, 9-($N^1$-methyl-$N^6$-(9-fluorenylmethyloxycarbonyl)-adeninyl)-, $N^1$-methyl-9-hypoxanthinyl-, 9-($N^1$-methyl-$N^2$-(9-fluorenylmethyloxycarbonyl)-guaninyl)-, etheno-9-adeninyl-, and etheno-1-cytosinyl-;

X is a linker chain of between $C_{1-100}$, selected from the group consisting of alkyl, alkenyl, cycloalkyl, aryl, and aralkyl, in a hydrocarbyl diradical moiety, optionally incorporating the intervening groups —O—, —S—, —S(O)$_2$—, —C(O)—, or —NR$_4$—, where $R_4$ is a hydrogen radical, or a substituted $C_1$ to $C_{20}$ alkyl or a substituted aralkyl, and connected to a solid support suitable for oligonucleotide synthesis;

W is a linker that contains an ester bond or an oxyethylsulfone group;

Z is controlled pore glass (CPG) or polystyrene;

$R_2$ is tert-butyl-dimethylsilyl group (TBDMS), triisopropylsilyl oxymethylene (TOM), 1-(2-fluorophenyl)-4-methoxypiperidiny-4-yl group (Fpmp), 1-(4-chlorophenyl)-4-methoxypiperidiny-4-yl (CPEP), tetrahydropyranyl group (THP) or O-bis(2-acetoxyethoxy)methyl group (ACE);

R is a cyanoethyl radical, alkyl radical or aryl radical; and wherein the process of synthesis of cyclic phosphate of formula 13A comprises the steps of:
  (a) providing a support attached nucleotide of formula 4 or formula 10;
  (b) detaching said nucleotide from the solid support under basic conditions and removing the base protecting group(s), if present, from the nucleotide; and
  (c) removing the sugar protecting group $R_2$ by application of a reagent selected from the group consisting of acetic acid N(C$_2$H$_5$)$_3$/nHF and Py/nHF, where n is a rational number, $1 \leq n \leq 3$.

9. The method of claim 8 wherein R is ribonucleotide or 2'-deoxyribonucleotide having a length of 2-100 covalently coupled nucleotides, optionally substituted by one or more nucleotides independently selected from the group consisting of 2'-O-methyl-ribonucleotides, 2'-deoxy-2'-fluoro-ribonucleotides, 2'-deoxy-2'-amino-ribonucleotides, 2'-O-(2-methoxyethyl)-ribonucleotides, 2'-O-allyl-ribonucleotides, 2'-O-propargyl-ribonucleotides, and 2'-O-butynyl-ribonucleotides.

* * * * *